US012784877B2

(12) United States Patent
Andersson et al.

(10) Patent No.: US 12,784,877 B2
(45) Date of Patent: Nov. 3, 2026

(54) METHODS AND DEVICES FOR DETERMINING BONDS IN PARTICLE TRAJECTORIES

(71) Applicant: Compular AB, Gothenburg (SE)

(72) Inventors: Rasmus Andersson, Älvängen (SE); Fabian Årén, Gothenburg (SE); Patrik Johansson, Gothenburg (SE)

(73) Assignee: Compular AB, Gothenburg (SE)

( * ) Notice: Subject to any disclaimer, the term of this patent is extended or adjusted under 35 U.S.C. 154(b) by 591 days.

(21) Appl. No.: 18/033,504

(22) PCT Filed: Jun. 17, 2021

(86) PCT No.: PCT/SE2021/050593

§ 371 (c)(1),
(2) Date: Apr. 24, 2023

(87) PCT Pub. No.: WO2022/093088

PCT Pub. Date: May 5, 2022

(65) Prior Publication Data

US 2023/0410951 A1 Dec. 21, 2023

(30) Foreign Application Priority Data

Oct. 26, 2020 (SE) .................................... 2051245-5

(51) Int. Cl.
*G16C 20/20* (2019.01)
*G16C 20/70* (2019.01)
*G16C 60/00* (2019.01)

(52) U.S. Cl.
CPC ............. *G16C 20/20* (2019.02); *G16C 20/70* (2019.02); *G16C 60/00* (2019.02)

(58) Field of Classification Search
CPC ........ G16C 20/20; G16C 20/70; G16C 60/00; G16C 10/00; G01N 15/10; G01N 33/00; G16B 15/00
See application file for complete search history.

(56) References Cited

U.S. PATENT DOCUMENTS

2007/0085850 A1* 4/2007 Hong ..................... G05B 19/41
345/442
2008/0243452 A1* 10/2008 Bowers ..................... G06F 9/30
703/2

(Continued)

FOREIGN PATENT DOCUMENTS

CN 108985375 A 12/2018
CN 110070918 A 7/2019

(Continued)

OTHER PUBLICATIONS

Koen E. Merkus, Single-Bond Association Kinetics Determined by Tethered Particle Motion: Concept and Simulations, p. 1612-1620, Biophysical Journal 111, 1612-1620, Oct. 18, 2016. (Year: 2016).*

(Continued)

*Primary Examiner* — Tung S Lau
(74) *Attorney, Agent, or Firm* — MARSHALL, GERSTEIN & BORUN LLP

(57) ABSTRACT

A method for determining bonds in particle trajectories, including the steps of obtaining a data set of particle trajectories in a material system, dynamically identifying bonds between particles in the material system, wherein dynamically identifying bonds includes selecting a candidate bond comprising a pair of particles, and determining the candidate bond as bound if: the pair of particles are closer than a predetermined maximum distance based on a combination of particle radii of the pair of particles over a first predetermined time period. During a second predetermined time period, an average distance between the pair of par- (Continued)

ticles is within a tolerance associated with at least one of: a peak of a partial radial distribution function or a measure of equilibrium bond length, or nearest neighbour distance of the pair of particles; and a first particle in the candidate bond is not present within an exclusion body associated with the second particle in the candidate bond and any other particle, or fulfils a bond-length criterion if being present within said exclusion body over a third predetermined time period.

10 Claims, 11 Drawing Sheets

(56) References Cited

U.S. PATENT DOCUMENTS

| | | | | |
|---|---|---|---|---|
| 2015/0186572 | A1 | 7/2015 | Ohnishi | |
| 2016/0004844 | A1 | 1/2016 | Matsumoto et al. | |
| 2016/0078155 | A1 | 3/2016 | Mochizuki et al. | |
| 2018/0372732 | A1 | 12/2018 | Brettschneider et al. | |
| 2019/0272468 | A1 | 9/2019 | Feinberg et al. | |
| 2024/0169124 | A1* | 5/2024 | Batson | G06F 9/5066 |
| 2024/0355413 | A1* | 10/2024 | Duplay | G16B 15/20 |

FOREIGN PATENT DOCUMENTS

| | | | |
|---|---|---|---|
| CN | 110234994 | A | 9/2019 |
| EP | 2899656 | A1 | 7/2015 |
| EP | 2921980 | A1 | 9/2015 |
| EP | 2977923 | A1 | 1/2016 |
| JP | 2005293296 | A | 10/2005 |

OTHER PUBLICATIONS

I. Jordanoff, Solid Third Body Analysis Using a Discrete Approach: Influence of Adhesion and Particle Size on Macroscopic Properties, 2002 by ASME, p. 530-538 (Year: 2002).*

Mihai V. Putz, The Bondons: The Quantum Particles of the Chemical Bond, Int. J. Mol. Sci. 2010, 11, 4227-4256; doi: 10.3390/ijms11114227 (Year: 2010).*

International Search Report and Written Opinion, International Application No. PCT/SE2021/050593, mailed Aug. 30, 2021.

Office Action, Swedish Application No. 2051245-5, dated Jun. 3, 2021.

Office Action, Swedish Application No. 2051245-5, dated Sep. 1, 2022.

Office Action, Swedish Application No. 2051245-5, dated Nov. 21, 2022.

Office Action, Chinese Application No. 202180072423.2, dated Feb. 6, 2026.

* cited by examiner

METHODS AND DEVICES FOR DETERMINING BONDS IN PARTICLE TRAJECTORIES

TECHNICAL FIELD

The present disclosure relates to a method for determining bonds and predicting forces in particle trajectories.

BACKGROUND ART

Many technologically relevant materials and liquids today are complex in terms of their intermolecular structure and dynamics, which is often disordered and/or dynamic. Even for simpler materials, their manufacturing and operation often involves some complexity.

The structure of a material system may be defined by e.g. the bonds between its constituent particles.

There are experimental methods in the market today that are directed to determining the structure and dynamics of material systems such as e.g. x-ray diffraction, vibrational spectroscopy, electric impedance spectroscopy and electrochemical techniques.

However, the mentioned experimental techniques fall short of confronting the complexity head on, i.e. they predict either very local or only crystalline structures. They do not, however, reliably and rapidly capture the explicit dynamics, the structures, and the bonds in between atoms in a material system. The same is true for quantum chemical modelling approaches such as Hartree-Fock theory, density functional theory, coupled cluster calculations etc. Molecular dynamics and similar techniques can capture atomic motion explicitly on the requisite scales but currently available analysis techniques cannot capture the emergent higher level (e.g. supramolecular) structures and their dynamics.

In complex material systems the atomic trajectories are often complex and challenging to analyse, especially with regards to supramolecular structure and dynamics. Accordingly, dynamically characterizing and identifying bonds in-between the atoms in a material system would allow for computing many of the physicochemical properties of the material system and understanding how they arise from the molecular scale dynamics.

Hence, there is a gap in the art for analysing disordered structure and dynamics of a system, more specifically there is a need for determining bonds in between atoms in a material system.

Thus, there is a need for determining bonds in atomic trajectories in a rapid, efficient and reliable manner in order to further predict the physicochemical properties of a material system. Accordingly, there is room for a method in the present art to explore the domain of providing a rapid, efficient and reliable method for determining bonds in material systems.

Even though some currently known solutions work well in some situations it would be desirable to provide methods and devices that fulfils the abovementioned requirements.

SUMMARY

It is therefore an object of the present disclosure to provide methods, and devices to mitigate, alleviate or eliminate one or more of the above-identified deficiencies and disadvantages.

This object is achieved by means of methods for determining bonds in particle (e.g. atom) trajectories, a computer-readable storage medium, and a device for the same.

The present disclosure provides a method comprising the steps of:

Firstly, obtaining a data set of particle trajectories in a material system e.g. a condensed matter system. Further, dynamically identifying bonds between particles in the material system. Dynamically identifying bonds comprises, selecting a candidate bond comprising a pair of particles and determining the candidate bond as bound if: The pair of particles are closer than a predetermined maximum distance based on a combination of particle radii of the pair of particles over a first predetermined time period and during a second predetermined time period, an average distance between the pair of particles is within a tolerance associated with at least one of a peak of a partial radial distribution function, pRDF, or a measure of equilibrium bond length, or nearest neighbour distance of the pair of particles. Furthermore, the candidate bond is bound if a first particle of the candidate bond is not present within an exclusion body associated with a second particle in the candidate bond and any other particle, or fulfils a bond-length criterion if being present within said exclusion body over a third predetermined time period. The exclusion body may be in the form of a three-dimensional half-infinite cone or a spherical sector.

The method provides the benefit of in a reliable and efficient manner determining the bonds in a material system. This has the benefits of forming the basis for an explicit representation of the system that can be used to study structure and dynamics in material systems. The method provides for a plurality of criteria that have to be fulfilled in order to determine a candidate bond as bound, this allows for high reliability and accuracy of the method. Further, the method allows for determining bonds relative to time periods which further provides for a more reliable and accurate method. The criteria take into account both distances between the particles of a candidate bond and the distance of any other particle relative to a candidate bond during time periods such to be suitable in a dynamic system.

The bond-length criterion may be fulfilled if a first length in-between the particles in the candidate bond is less than a predetermined factor multiplied with a second length, wherein the second length is defined by the distance in-between the pair of particles associated with the exclusion body.

Thus, allowing for further means of providing reliability in the determining of particle bonds. This prevents a scenario where the candidate bond may be mistakenly determined as not bound by being present in the exclusion body. By also taking a bond-length criterion into account in situations where the candidate bond is within the exclusion body, the reliability and accuracy of the method is further improved.

The method may further comprise the step of determining a bond lifetime if the candidate bond is determined as bound.

A benefit of this is that it allows the method to take into account the complexity and the dynamic character of a material system. The determining of the bond lifetime allows the method to provide further means for deriving the physicochemical properties of a system.

The method may further comprise the step of determining at least one bond graph based on the identified bonds in the material system. The at least one bond graph may be a time-dependent bond graph.

A benefit of determining at least one bond graph is that it allows for a detailed representation and classification of the structures present in a material system, and the different types of particles, where the location in the bond graph is also included in the definition of a type.

The method may further comprise the steps of characterizing local or global structures based on a partitioning of at least one bond graph and predicting the physicochemical properties of the material system based on the local or global structures.

This provides the benefit of allowing for a representation of the structures which is convenient to analyse/work with further, and which uniquely facilitates understanding of structure, dynamics and physicochemical properties arising from supramolecular structures and interactions.

The bond graph may be partitioned into subgraphs according to a first representation model or a second representation model, wherein the first representation model comprises partitioning a bond graph into connected components, and the second representation model comprises partitioning a bond graph into extended neighbourhoods defined as all vertices and edges up to a maximum graph distance from at least one of a central particle or motif.

A benefit of this is that the bond graph may be more conveniently arranged by partitioning it into different representation models that correspond to specific exemplars of structures, and that the exemplars can be classified into different types, which can be studied across exemplars. For instance, each representation model may be directed to a specific type of structure such as a percolating network or small isolated components, or the representation models may complement each other enabling a deeper understanding of a single material system.

The average distance d' (see FIG. 4*a*-4*b*) between a pair of particles may fulfil $$(1-\alpha)r_{peak} \le \frac{1}{T}\int_t^{t+T} d_{ij}(t)dt \le (1+\alpha)r_{peak},$$

wherein $\alpha$ is the tolerance, $r_{peak}$ is a peak in the partial radial distribution function, pRDF, or other measure of equilibrium bond length or nearest neighbour distance, and $d_{ij}(t)$ is the distance as function of time, t.

A benefit of this is that the average distance d' is derived by also having time and a tolerance as a factor making it more suitable for a complex dynamic system.

The partial radial distribution function, pRDF may be defined by $$g_{ij}(r) = \frac{1}{n_0}\frac{n(r)}{4\pi r^2},$$

wherein n(r) is the number density of neighbours of type j on distance r from particles of type i and the expression is normalised by the average bulk number density, $n_0$ of type j.

There is also provided a computer-readable storage medium storing one or more programs configured to be executed by one or more control circuitry of an electronic device, the one or more programs including instructions for performing the method as disclosed herein.

There is also provided an electronic device, comprising one or more control circuitry; and memory storing one or more programs configured to be executed by the one or more control circuitry, the one or more programs including instructions for performing the method as disclosed herein.

According to some aspects of the present disclosure there is also provided a method for determining bonds in particle trajectories, the method comprising the steps of obtaining a data set of particle trajectories in a material system. Further, the method comprises the step of dynamically identifying bonds between particles in the material system. Further, the method comprises determining at least one bond graph based on the identified bonds in the material system. Furthermore, the method comprises characterizing at least one interaction type for at least one particle in said at least one bond graphs based on a partitioning of the at least one bond graph. Moreover, the method provides a pre-defined scheme comprising average force-field data, the average force-field data being data relating to a force-field model acting on particles of each characterized interaction type.

An advantage of the method is that it provides a cost-effective method that is able to predict the forces acting on the particles in systems without explicitly computing expensive long-range interactions, whilst retaining the accuracy of the (training) data. Furthermore, this enables to propagate particle trajectories in time. Further, the method may determine bonds in particle trajectories in an accurate and rapid manner both real-time in a system and also for future time points in said system.

The pre-defined scheme may be a look-up table, function or any other form of look-up model. Thus, after identifying each interaction type, the method may provide and determine by means of the pre-defined scheme average force-field data of the specific interaction.

The method may further comprise the step of propagating trajectories of the identified bonds in the material system, based on the pre-defined scheme.

The step of dynamically identifying bonds between particles in the material system may comprise selecting a candidate bond comprising a pair of particles. Further, determining the candidate bond as bound if:

i. the pair of particles are closer than a predetermined maximum distance based on a combination of particle radii of the pair of particles over a first predetermined time period;
ii. during a second predetermined time period (t2), an average distance (d') between the pair of particles (10, 11) is within a tolerance (t') associated with at least one of: a peak of a partial radial distribution function, pRDF, or a measure of equilibrium bond length, or nearest neighbour distance of the pair of particles (10, 11); and
iii. a first particle (10) of the candidate bond is not present within an exclusion body (15) associated with a second particle (11) in the candidate bond and any other particle (12), or fulfils a bond-length criterion if being present within said exclusion body (15) over a third predetermined time period (t3).

Further, the average force-field data for each interaction type may be derived/obtained/determined from a distribution of generalised forces over a generalised force-field-describing coordinate, wherein each interaction type is associated to at least one generalised force-field-describing coordinate.

In other words, for each interaction type that is identified, the method may obtain a distribution of generalised forces for the specific interaction type, wherein the method determines an average value or a data set of average values from said distribution.

The average distribution may be at least one of a mean value of the distribution of forces, a modal value of the distribution of forces or a median value of the distribution of forces or any combination thereof.

The propagating step may comprise time integrating the material system from a first time point to a second time point. Thus allowing the method to accurately simulate future states of the material system.

The interaction types may be at least one of a 2-body bonded or non-bonded, 3-body bonded or non-bonded, 4-body bonded or non-bonded and n-body bonded or non-bonded interaction, where n is an arbitrary non-negative integer. Accordingly, the method provides the advantage of identifying a plurality of different interaction types, as well as identifying non-bonded interactions. Resulting in a more accurate method. The interaction types may also be any other suitable interaction type.

The method may further comprise the step of: using the force field data to generate a smoothing function dependent on at least one generalised force-field-describing coordinate.

BRIEF DESCRIPTION OF THE DRAWINGS

In the following the disclosure will be described in a non-limiting way and in more detail with reference to exemplary embodiments and tests illustrated in the enclosed drawings, in which.

DETAILED DESCRIPTION

Figure 1:
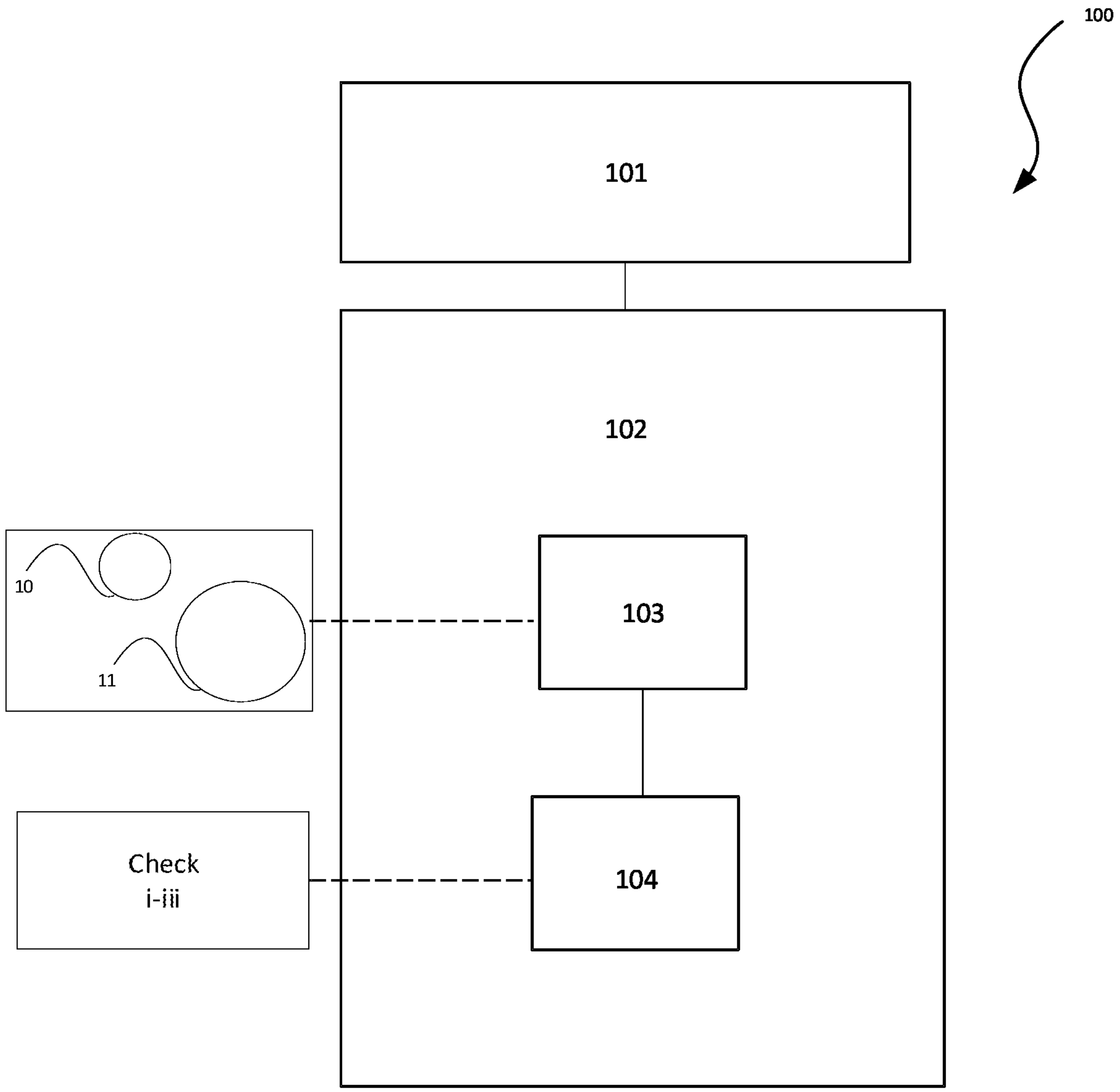
FIG. 1 Illustrates a method for determining bonds in particle trajectories in the form of a flowchart in accordance with an embodiment of the present disclosure.

In the following detailed description, some embodiments of the present disclosure will be described. However, it is to be understood that features of the different embodiments are exchangeable between the embodiments and may be combined in different ways, unless anything else is specifically indicated. Even though in the following description, numerous specific details are set forth to provide a more thorough understanding of the provided method and devices, it will be apparent to one skilled in the art that the method and devices may be realized without these details. In other instances, well known constructions or functions are not described in detail, so as not to obscure the present disclosure.

In the following description of example embodiments, the same reference numerals denote the same or similar components.

In the present disclosure, both particle, material system, and bond are defined in their widest possible sense. A particle may be any quantity of matter that can be assigned a centre-of-mass position at any point in time including but not limited to atoms, ions, electrons, holes, molecules, functional groups, beads, grains, colloids, vesicles, and rigid bodies. A material system may be any system consisting of a number of interacting particles. A bond between a pair of particles may be an interaction that results in that they move together as a cohesive unit. In the notion of interaction, also effective interactions such as steric effects may be comprised, the aggregate effect of interactions between other particles, or even correlation in space and time due to initial conditions or external causes. Types of bonds include but are not limited to: covalent bonds, ionic bonds, metallic bonds, van der Waals interactions, steric constraints, any form of adhesion and any form of electromagnetic interaction. It is often challenging to capture the structure and dynamics of complex material systems, or complex processes even in simpler material systems. The present disclosure may be directed to condensed matter systems of atoms, ions and molecules, but may also be applied equally to the broader categories of particles, interactions and material systems as described herein.

The term "bond candidacy time" refers to a time period during which it is conceivable that a pair of particles are bound based on their distance being relatively small.

The term "distance averaging time" refers to a time period (subset of bond candidacy time) over which it makes sense to calculate the time average distance of a pair of particles without biasing the average towards larger values due to the possible initial approach and final departure of the pair towards and away from each other.

The term "bond exclusion time" refers to a time period over which it is determined whether a candidate bond is on average within any exclusion bodies.

The term "bond lifetime" refers to the time period between a bond forming (i.e. being determined as bound) and breaking.

The term "motif" refers to a single particle or group of particles which may have defined internal bond graph topology.

The term "material system" refers to a system consisting of a number of particles interacting or effectively interacting in some way, including but not limited to in a solid or liquid state. The material systems as disclosed herein may be a condensed matter system.

FIG. 1 illustrates a method 100 for determining bonds in accordance with an embodiment of the present disclosure. The method 100, comprises the steps of: obtaining 101 a data set of particle trajectories in a material system, and dynamically identifying bonds 102 between particles in the material system, wherein the step of dynamically identifying bonds 102 comprises: selecting 103 a candidate bond comprising a pair of particles 10, 11. Determining 104 the candidate bond as bound if (see FIGS. 3-5 for details relating to i-iii):

i. the pair of particles 10, 11 are closer than a predetermined maximum distance $d^{max}$ (see FIG. 3*a-b*) based on a combination of particle radii r1, r2 (shown in FIG. 3*a*-3*b*) of the pair of particles over a first predetermined time period t1;

ii. during a second predetermined time period t2, an average distance d' between the pair of particles 10, 11 is within a tolerance t' associated with at least one of: a peak of a partial radial distribution function, pRDF, or a measure of equilibrium bond length, or nearest neighbour distance of the pair of particles 10, 11; and iii. a first particle 10 in the candidate bond is not present within an exclusion body 15 associated with a second 11 particle in the candidate bond and any other particle 12, or fulfils a bond-length criterion if being present within said exclusion body 15 over a third predetermined time period t3.

The term "criteria" refers to the three steps that are to be fulfilled to determine a candidate bond as bound in accordance with the determining 104 step. The criteria are denoted i-iii in the present disclosure.

The term "particle" may refer to an atom. Accordingly, the method may be directed to identify bonds between atoms in a material system. Thus, the pair of particles 10, 11 shown in FIG. 1 may be a pair of atoms.

The first predetermined time period t1 may be a bond candidacy time which is defined as a time period during which it is conceivable that a pair of particles 10, 11 are bound based on their distance being below a cut-off.

Figure 4A:
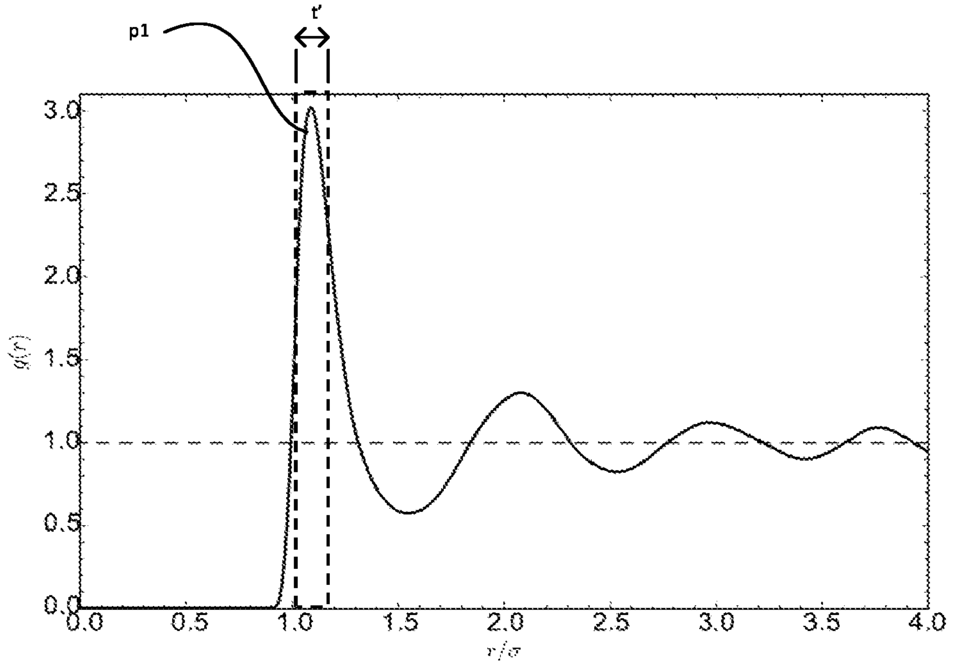
FIG. 4*a* Illustrates an example of a partial radial distribution function of a pair of particles related to the criteria ii.
Figure 4B:
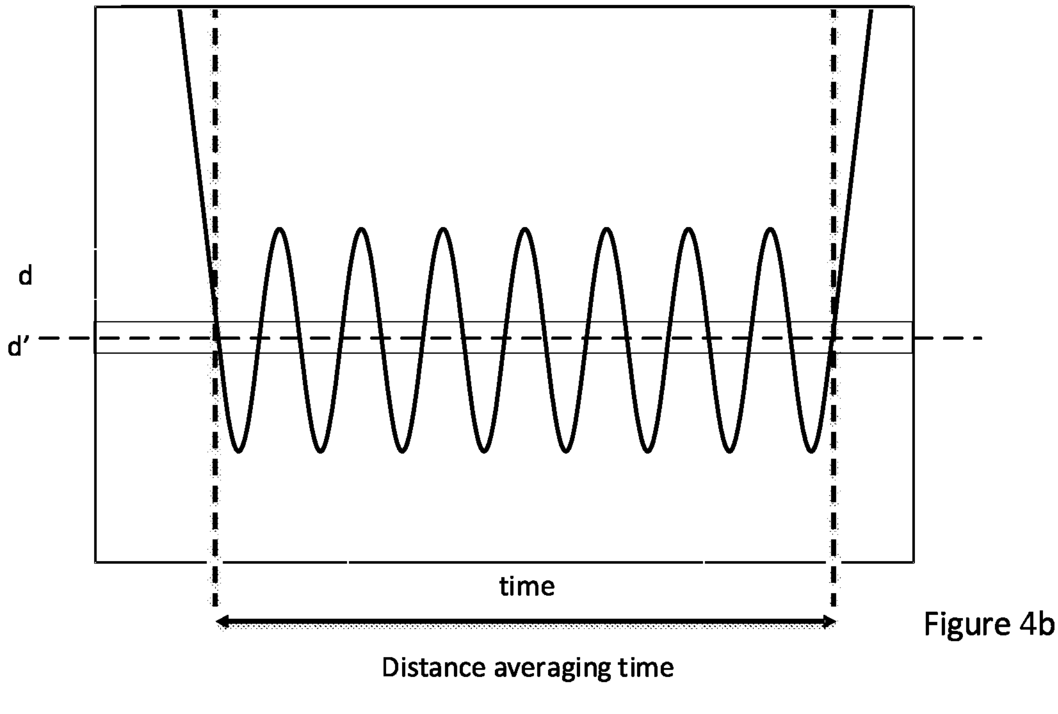
FIG. 4*b* illustrates a graph showing a pair of particles being within a tolerance of the pRDF in FIG. 4*a;*

The second predetermined time period t2 may be the distance averaging time which is defined as a time period (subset of bond candidacy time) over which the time average distance of a pair of particles 10, 11 is calculated without biasing the average towards larger values due to the possible initial approach and final departure of the pair towards and away from each other (shown in FIG. 4*b*).

The third predetermined time period t3 may be the bond exclusion time which is defined by a time period over which it is determined whether a candidate bond 10, 11 is on average within any exclusion bodies.

The steps of dynamically identifying bonds 102 may be performed iteratively such to identify a plurality of bonds during a longer time period. Further, the method 100 may select 103 a plurality of candidate bonds and perform the determining step 104 simultaneously on independent candidate bonds.

Figure 2:
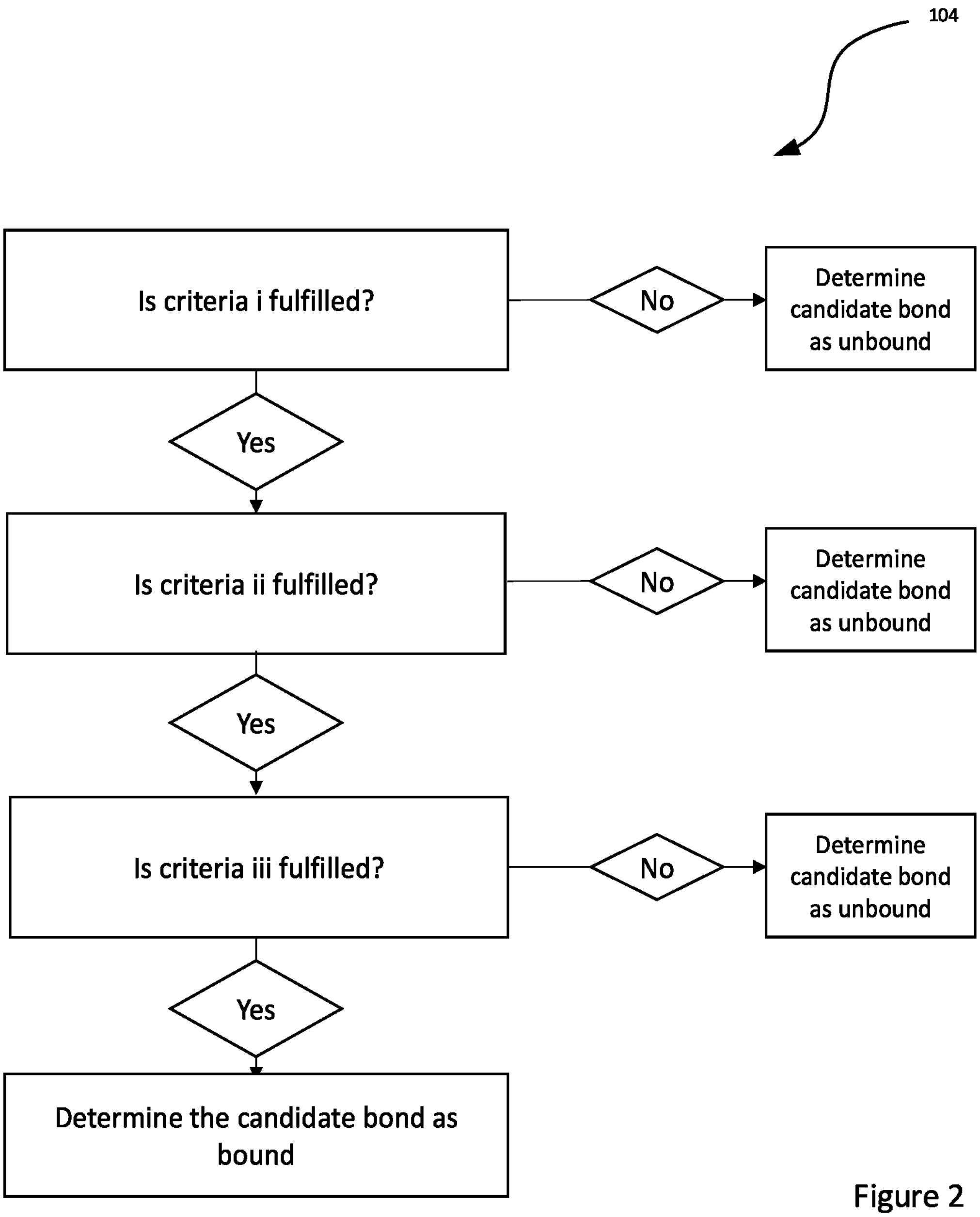
FIG. 2 Illustrates the step of determining a candidate bond as bound in the form of a decision tree.

FIG. 2 discloses the step of determining 104 the candidate bonds as bound in more detail in the form of a decision tree performed by the method 100. As seen in FIG. 2, the criteria/conditions i-iii have to be fulfilled in order to determine a candidate bond 10, 11 as bound. Further, in FIG. 2 the criteria i-iii need to be fulfilled in a specified order in order to determine a candidate bond as bound. However, according to some embodiments, the criteria i-iii may be fulfilled in an arbitrary order.

Figure 3A:
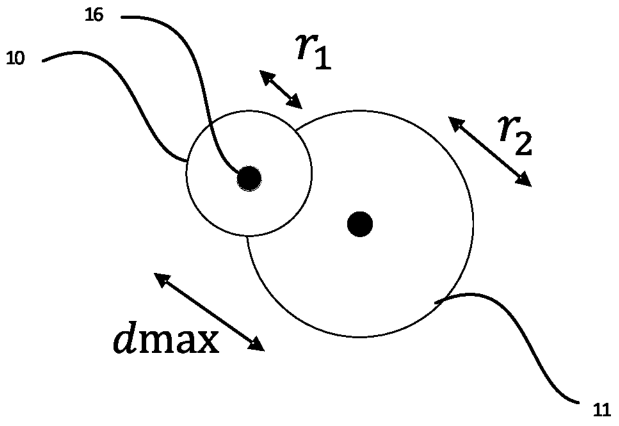
FIG. 3*a* Illustrates a pair of particles in a scenario where a criteria i is fulfilled.
Figure 3B:
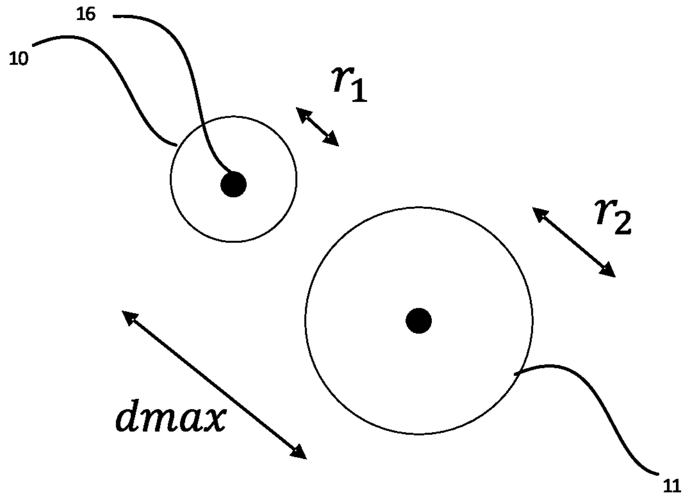
FIG. 3*b* Illustrates a pair of particles in a scenario where a criteria i is not fulfilled.

FIGS. 3*a* and 3*b* illustrates the criteria i in the step of determining 104 in more detail, showing a first scenario in FIG. 3*a* where the pair of particles are closer than a predetermined maximum distance $d^{max}$ based on a combination of particle radii, r1, r2 of the pair of particles over a first predetermined time period i.e. FIG. 3*a* fulfils $d^{max}<C(r_1+r_2)$. C may be a factor in the range of 0.1-10. The particle radii r1, r2 may be the van der Waals radii, ionic radii, covalent radii, metallic radii or based on a cut-off of the electron density FIG. 3*b* shows a second scenario where i is not fulfilled. In other words, the particles 10, 11 in FIG. 3*a* may be bound since passing i of the criteria in the determining step 104. However, in FIG. 3*b* the particles 10, 11 may be concluded to be unbound since not fulfilling the criteria i. Thus in FIG. 3*b*, $d^{max}<C(r_1+r_2)$.

FIG. 4*a* illustrates a part of criterion ii in the step of determining 104 where there is seen a partial radial distribution function of the pair of particles (i.e. the candidate bond). Thus, if an average distance d' between the pair of particles is within a tolerance t' associated with the peak p1 of the pRDF seen in FIG. 4 the criteria ii is fulfilled. It is seen in FIG. 4*b* that the average distance d' is within the tolerance referred to in FIG. 4*a*. Accordingly, in a scenario where the average distance d' is not within the tolerance t' referred to in FIG. 4*a*, the candidate bond is determined as not bound. The tolerance t' may be associated with the first peak of the pRDF. The tolerance may be defined by 1-200% of the half-width at half maximum of the pRDF.

Figure 5:
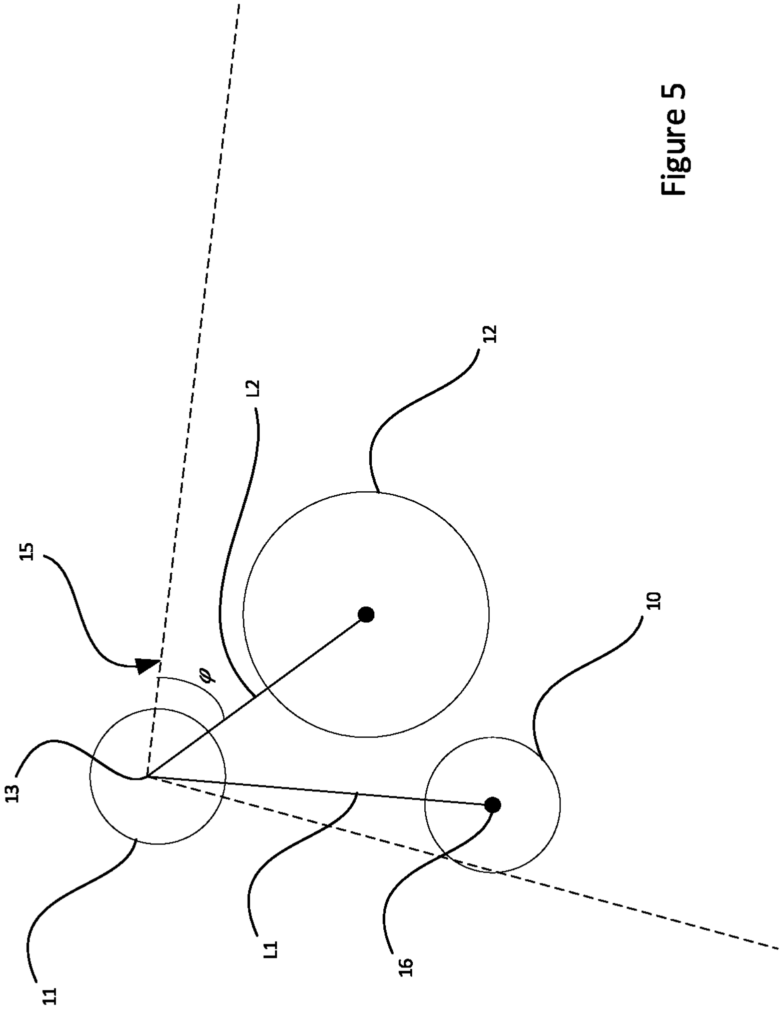
FIG. 5 illustrates an exclusion cone, a candidate bond and another particle related to the criteria iii.

FIG. 5 illustrates a scenario relating to the criterion iii in the step of determining 104, where there is seen a candidate bond 10, 11 and an exclusion body 15 associated with one of the particles 11 in the candidate bond and any other particle 12. It should be noted that the candidate bond 10, 11 may still be bound if it is present in the exclusion body 15 but fulfils a bond-length criterion. The other particle 12 may be another particle that is bound to one of the particles in the candidate bond 10, 11. The other particle 12 may be another particle that previously has been determined as bound by means of the method 100. The exclusion body 15 is three-dimensional (not explicitly seen in FIG. 5). Further, the term "body" is preferably a semi-infinite cone (as seen in FIG. 5) but may be in any other suitable form such as a cone with finite height or a spherical sector. As seen in FIG. 5, the exclusion cone 15 may be defined by having a tip 13 associated with the centre of one of the candidate particles 11, an axis (not explicitly shown, but is in in the direction of L2) in the direction of a particle 12 other than the candidate particle 10, further having a predetermined angle. The angle may be within the range of 30-120°.

The bond-length criterion is fulfilled if a first length L1 in-between the particles 10, 11 in the candidate bond 10, 11 is less than a predetermined factor multiplied with a second length L2, wherein the second length L2 is defined by the length in-between the pair of particles 11, 12 associated with the exclusion body 15. The factor may be in the range of 1.0-2.0. In FIG. 5, the first particle 10 is within the exclusion cone 15, thus the criteria iii may only be fulfilled if the first length L1 in-between the particles 10, 11 in the candidate bond is less than a predetermined factor multiplied with the second length L2. Particles may be defined as being within the exclusion cone if a centre of mass 16 of a particle is within the exclusion cone.

Figure 6:
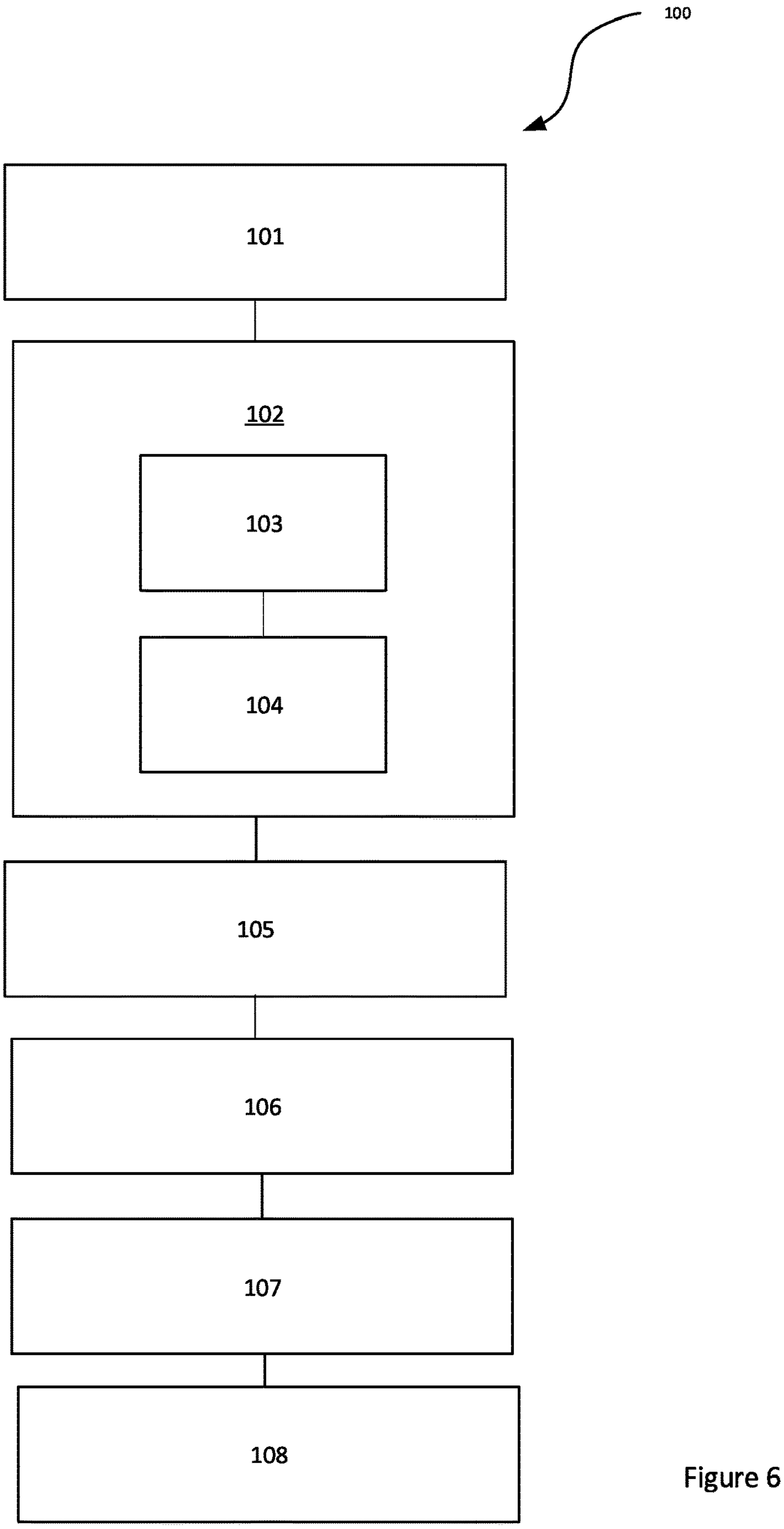
FIG. 6 illustrates a method for determining bonds in particle trajectories in the form of a flowchart in accordance with an embodiment of the present disclosure.
Figure 7:
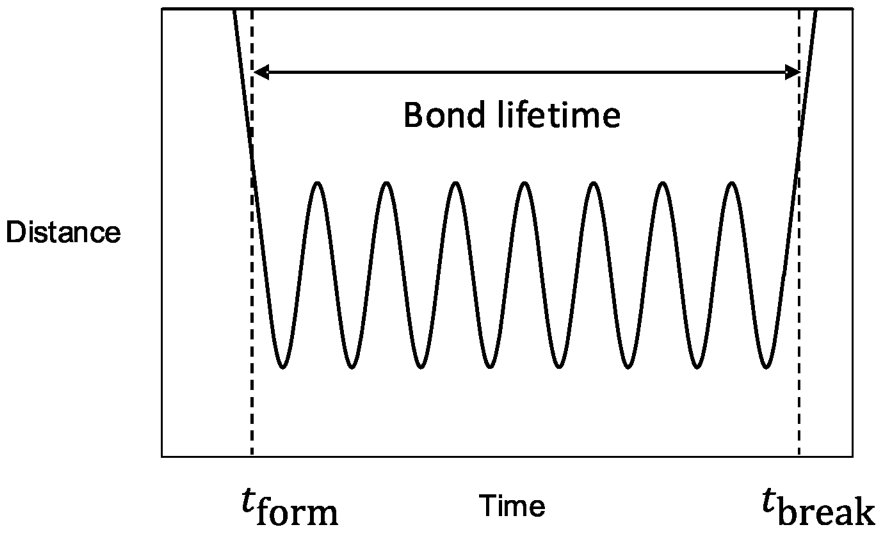
FIG. 7 illustrates a graph showing the bond lifetime.

FIG. 6 illustrates the method 100 further comprising the step of determining 105 a bond lifetime if the candidate bond 10, 11 is bound. The bond lifetime may be determined by starting from the bond averaging time and extending it in both directions until the distance is greater or equal to the greatest distance within the bond averaging time (shown in FIG. 7).

Referring back to FIG. 6, there is further illustrated the method 100 further comprising the step of determining 106 at least one bond graph based on the identified bonds in the material system. FIG. 6 further shows the method comprising the step of characterizing 107 local structures based on a partitioning of at least one bond graph and further predicting 108 the physicochemical properties of the material system based on the local structures.

The bond graph may be partitioned according to a first representation model or a second representation model, wherein the first representation model comprises partitioning a bond graph into connected components, and the second representation model comprises partitioning a bond graph into graph neighbourhoods defined by a maximum graph distance from at least one of a central particle or motif.

The term "extended neighbourhood" refers to a subgraph of a larger graph, where all vertices up to a predetermined graph distance from a central motif and the edges between these vertices are included.

The term "bond graph" refers to a graph having vertices, where the vertices are particles or groups of particles and the edges, which may be undirected, are the bonds between them.

The term "graph distance" is defined as the minimum number of edges needed to connect two vertices in a graph.

The average distance d' between a pair of particles may fulfil $$(1-\alpha)r_{peak} \le \frac{1}{T}\int_{t}^{t+T} d_{ij}(t)dt \le (1+\alpha)r_{peak}$$

wherein α is the tolerance t', $r_{peak}$ is a peak in the partial radial distribution function, pRDF, or other measure of equilibrium bond length or nearest neighbour distance, and $d_{ij}(t)$ is a distance as function of time, t.

Further, the partial radial distribution function, pRDF may be defined by $$g_{ij}(r) = \frac{1}{n_0}\frac{n(r)}{4\pi r^2},$$

wherein n(r) is the number density of particles or motifs of type j on distance r from particles of type i and the expression is normalised by the average bulk number density, $n_0$ of type j.

Figure 8:
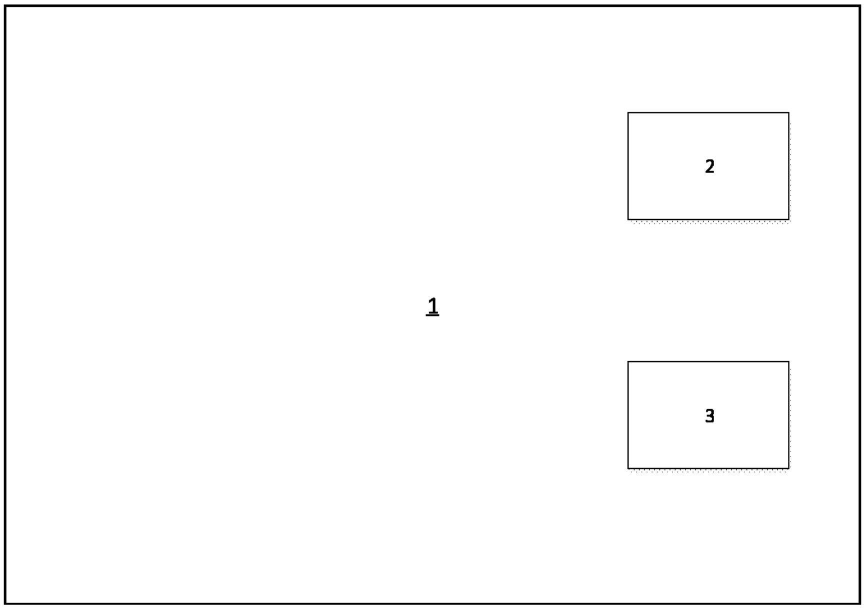
FIG. 8 schematically illustrates an electronic device in accordance with an embodiment of the present disclosure.

FIG. 8 schematically depicts an electronic device 1, comprising control circuitry 2; and a memory device 3 storing one or more programs configured to be executed by the one or more control circuitry 2, the one or more programs including instructions for performing the method 100 as disclosed herein.

The memory device 2 may comprise any form of volatile or non-volatile computer readable memory including, without limitation, persistent storage, solid-state memory, remotely mounted memory, magnetic media, optical media, random access memory (RAM), read-only memory (ROM), mass storage media (for example, a hard disk), removable storage media (for example, a flash drive, a Compact Disk (CD) or a Digital Video Disk (DVD)), and/or any other volatile or non-volatile, non-transitory device readable and/or computer-executable memory devices that store information, data, and/or instructions that may be used by each associated control circuitry 2. The memory device 3 may store any suitable instructions, data or information, including a computer program, software, an application including one or more of logic, rules, code, tables, etc. and/or other instructions capable of being executed by the control circuitry and, utilized. Memory device 3 may be used to store any calculations made by control circuitry 2 and/or any data received via interface. In some embodiments, each control circuitry 2 and each memory device 3 may be considered to be integrated Each memory device 3 may also store data that can be retrieved, manipulated, created, or stored by the control circuitry 2. The data may include, for instance, local updates, parameters, training data for optimizing the method 100 as disclosed herein, learning models and other data. The data can be stored in one or more databases. The one or more databases can be connected to the server by a high bandwidth field area network (FAN) or wide area network (WAN), or can also be connected to server through a communication network.

The control circuitry 2 may include, for example, one or more central processing units (CPUs), graphics processing units (GPUs) dedicated to performing calculations, and/or other processing devices.

The memory device 3 can include one or more computer-readable media and can store information accessible by the control circuitry including instructions/programs that can be executed by the control circuitry 2.

The instructions which may be executed by the control circuitry 2 may comprise instructions for performing the method 100 according to any aspects of the present disclosure. Each control circuitry 2 may be configured to perform any of the steps as disclosed in the present disclosure such as the steps in the methods 100.

There is further provided a computer-readable storage medium storing one or more programs configured to be executed by one or more control circuitry of an electronic device 1, the one or more programs including instructions for performing the method 100 as disclosed herein. The electronic device may be the electronic device in FIG. 8.

Figure 9:
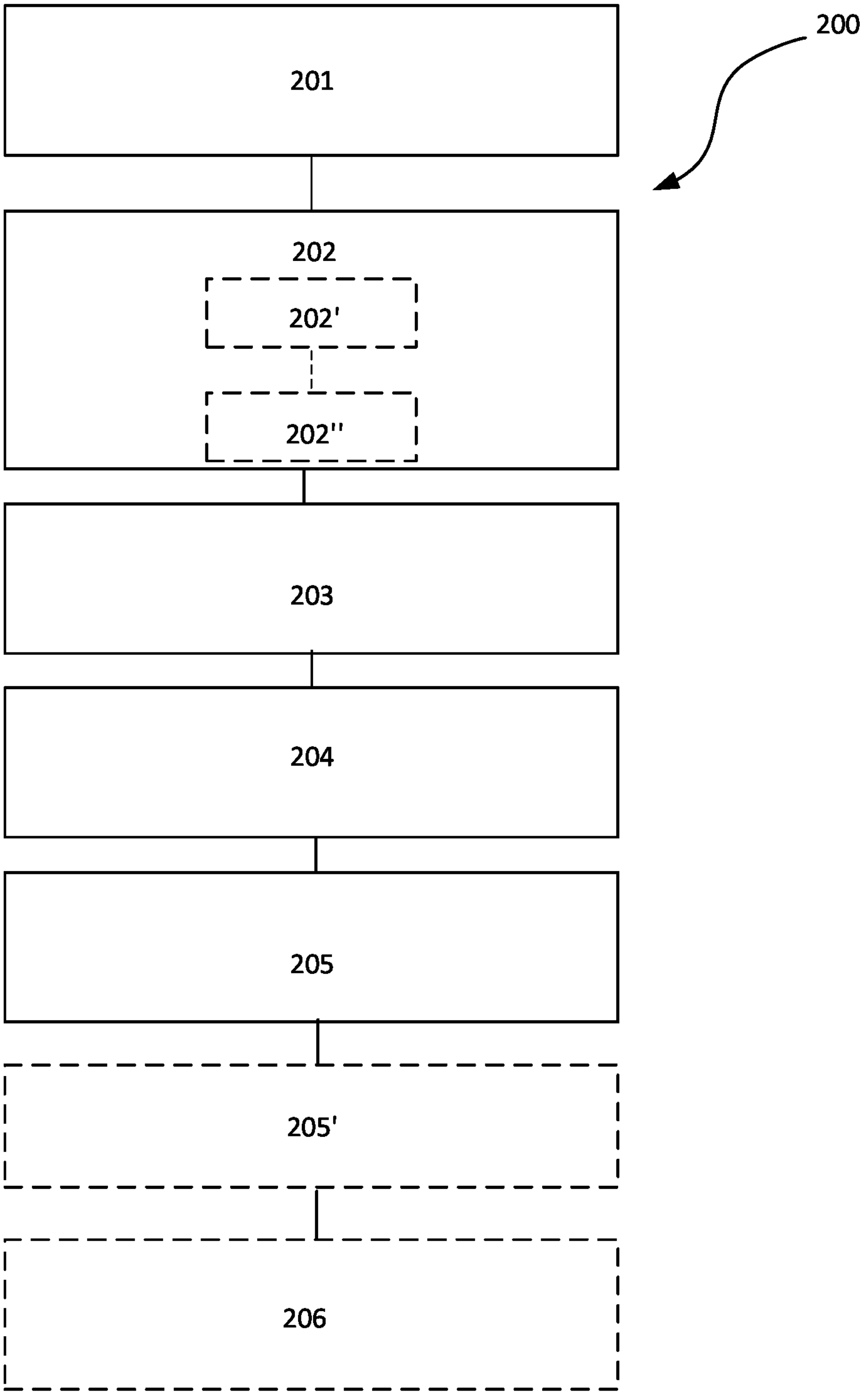
FIG. 9 schematically illustrates a method for determining bonds in particle trajectories in the form of a flowchart in accordance with an aspect of the present disclosure.

FIG. 9 illustrates a method 200 for determining bonds (and predicting forces) in particle trajectories in accordance with an aspect of the present disclosure. The method 200, comprising the steps of obtaining 201 a data set of particle trajectories in a material system, dynamically identifying bonds 202 between particles in the material system. Further, the method 200 comprises determining 203 at least one bond graph based on the identified bonds in the material system. Further, the method 200 characterizes 204 at least one interaction type for at least one particle in said at least one bond graphs based on a partitioning of the at least one bond graph. Moreover, the method provides 205 a pre-defined scheme comprising average force-field data, the average force-field data being data relating to a force-field acting on particles of each characterized interaction type. Furthermore, the method 200 may also comprise the step of propagating 206 trajectories of the identified bonds in the material system, based on the pre-defined scheme.

FIG. 9 also illustrates that the step of dynamically identifying bonds 202 between particles in the material system may comprise selecting 202' a candidate bond comprising a pair of particles, and determining 202" the candidate bond as bound if specific criterias are fulfilled.

As illustrated in FIG. 9. the method 200 may further comprise the step of: using (205'), by means of one or more learning algorithms, statistical methods, interpolation methods, extrapolation methods or any combination thereof, the force field data to generate a smoothing function dependent on at least one generalised force-field-describing coordinate. The learning algorithms, statistical methods, interpolation methods or extrapolation methods may be based on Bayesian learning, neural networks, linear regression, non-linear regression, maximum likelihood methods, a combination thereof or any other suitable method.

The criteria that are to be fulfilled are shown in detail in FIG. 2-5 and may disclose the same steps, means and advantages as previously discussed within the present disclosure, criteria being:

i. the pair of particles (10, 11) are closer than a predetermined maximum distance based on a combination of particle radii (r1, r2) of the pair of particles (10, 11) over a first predetermined time period (t1);

ii. during a second predetermined time period (t2), an average distance (d') between the pair of particles (10, 11) is within a tolerance (t') associated with at least one of: a peak of a partial radial distribution function, pRDF, or a measure of equilibrium bond length, or nearest neighbour distance of the pair of particles (10, 11); and iii. a first particle (10) of the candidate bond is not present within an exclusion body (15) associated with a second particle (11) in the candidate bond and any other particle (12), or fulfils a bond-length criterion if being present within said exclusion body (15) over a third predetermined time period (t3).

Figure 10:
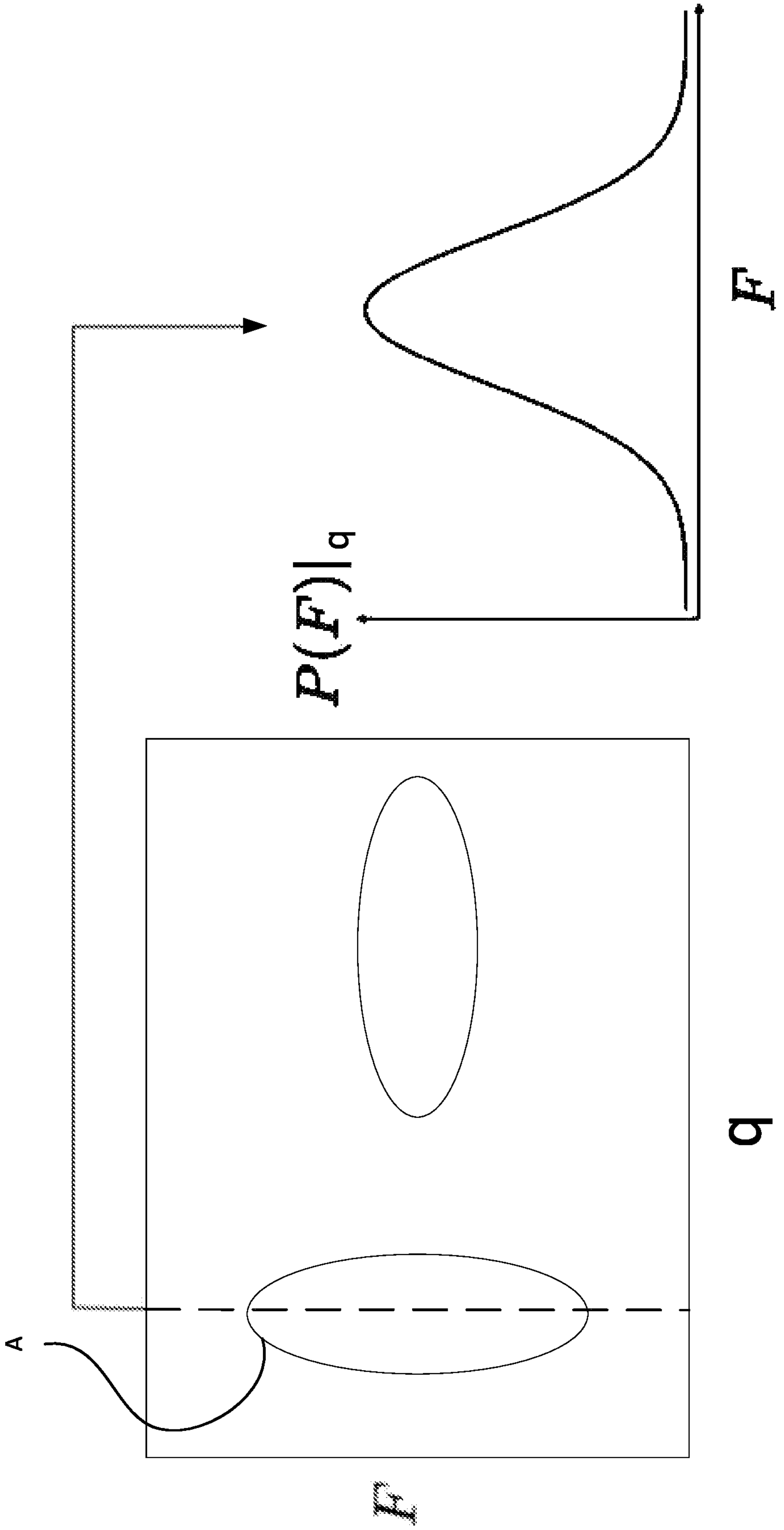
FIG. 10 illustrates a plot for a generalised coordinate and a distribution of forces for all values of said coordinate.

FIG. 10 illustrates a schematic of a generalised force associated to an interaction type described by a generalised coordinate q. For every value of the coordinate q, a distribution of forces, F exist, that may be assumed to be Gaussian. Accordingly, for all values of q, there exists a distribution, collectively forming a 2D histogram. In other words, the histogram is a projection/distribution of generalized forces acting on all particles partaking in an interaction type against a generalized coordinate q describing said interaction. Based on the 2D histogram an average value may be determined and stored in a look-up table, which may or may not be used to generate a smooth function, through e.g. Bayesian learning, neural networks, or linear or non-linear regression, so that for each interaction type there is an average value (or set of values) stored which may then used to propagate the material system. In accordance with the present disclosure, the look-up table may correspond to the pre-determined scheme. Accordingly, the combination of interaction types, average force-field value allows for propagation of the system. The denoted reference letter A, refers to a collection of generalised force distributions F.

The term "force-field" may refer to the types of forces between atoms within all types of bonded and non-bonded interactions, including their look-up representation. Thus, it may refer to stretch force, bending force, proper-, and improper torsion forces, van der Waals force, electrostatic force or other force terms, as well as any combination thereof.

The average force-field data for each interaction type is derived from a distribution of generalised forces over a generalised force-field-describing coordinate, wherein each interaction type is associated to at least one generalised force-field-describing coordinate.

The average force-field data may be at least one of a mean value of the distribution of forces, a modal value of the distribution of forces or a median value of the distribution of forces or any combination thereof. The data may be a set of mean values, a set of modal values or a set of median values.

The step of propagating 206 may comprise time integrating the material system from a first time point to a second time point.

The interaction types may be at least one of a 2-body bonded or non-bonded, 3-body bonded or non-bonded, 4-body bonded or non-bonded and n-body non-bonded interaction, wherein n is an arbitrary non-negative integer. In other words, the interaction types may be interactions between a first atom and at least one additional atom.

Figure 11:
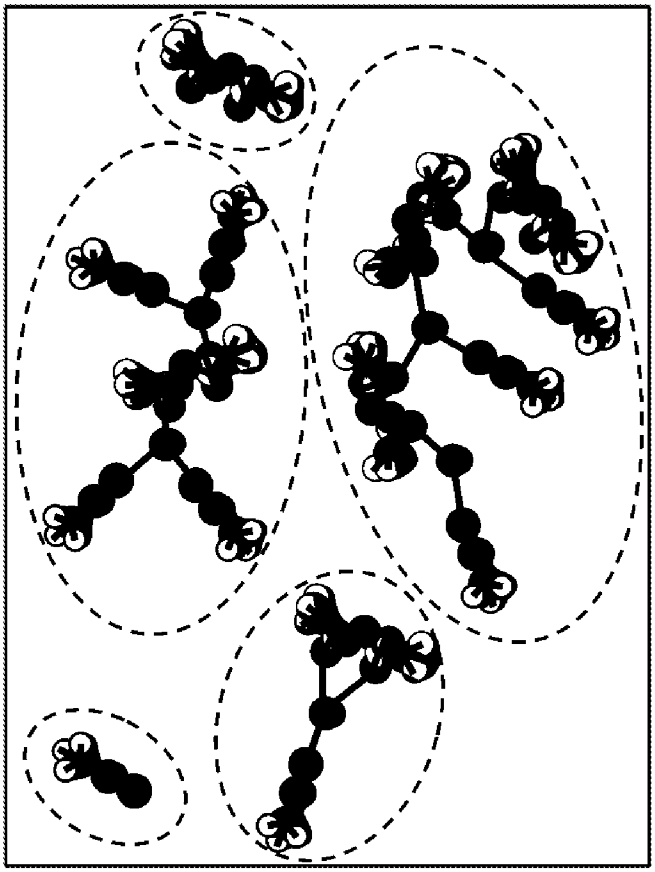
FIG. 11 illustrates a bond graph in accordance with an embodiment of the present disclosure.

FIG. 11 illustrates a bond graph in accordance with some embodiments, wherein the bonds are dynamically identified in particle trajectories of a material system and shown in said bond graph. The bond graph shown in FIG. 11 is a simplified view for illustration purpose and is not limiting for the present disclosure.

The invention claimed is:

1. A method for determining bonds between particles in particle trajectories performed by a control circuitry of an electronic device, the method comprising the steps of:

obtaining, in the control circuitry, a data set of particle trajectories in a material system;

dynamically, in the control circuitry, identifying bonds between particles in the material system, wherein dynamically identifying bonds comprises:

selecting a candidate bond comprising a pair of particles;

determining whether the candidate fulfills criteria comprising:

i. the pair of particles are closer than a predetermined maximum distance based on a combination of particle radii of the pair of particles over a first predetermined time period;

ii. during a second predetermined time period, an average distance between the pair of particles is within a tolerance associated with at least one of: a peak of a partial radial distribution function, or a measure of equilibrium bond length, or nearest neighbor distance of the pair of particles; and iii. a first particle of the candidate bond is not present within an exclusion body associated with a second particle in the candidate bond and any other particle, or fulfils a bond-length criterion if being present within said exclusion body over a third predetermined time period; and determining, in the control circuitry, the candidate bond as bound in response to determining that the candidate bond fulfills said criteria; and using, in the control circuitry, the determined bond to predict physiochemical properties of said material system.

2. The method according to claim 1, wherein the bond-length criterion is fulfilled if a first length in-between the particles in the candidate bond is less than a predetermined factor multiplied with a second length, wherein the second length is defined by the length in-between the pair of particles associated with the exclusion body.

3. The method according to claim 1, further comprising the step of:

determining a bond lifetime if the candidate bond is bound.

4. The method according to claim 1, further comprising the step of:

determining at least one bond graph based on the identified bonds in the material system.

5. The method according to claim 4, further comprising the steps of:

characterizing particle types or local or global structures based on a partitioning of at least one bond graph; and predicting the physicochemical properties of the material system based on the particle types or local or global structures.

6. The method according to claim 4, wherein a bond graph is partitioned according to a first representation model or a second representation model, wherein the first representation model comprises partitioning a bond graph into connected components, and the second representation model comprises partitioning a bond graph into graph neighborhoods defined by the vertices up to a maximum graph distance from at least one of a central particle or motif and the edges between them.

7. The method according to claim 1, wherein the average distance between a pair of particles fulfils $$(1-\alpha)r_{peak} \leq \frac{1}{T}\int_{t}^{t+T} d_{ij}(t)dt \leq (1+\alpha)r_{peak}$$

wherein $\alpha$ is the tolerance, $r_{peak}$ is a peak in the partial radial distribution function, or other measure of equilibrium bond length or nearest neighbour distance, and $d_{ij}(t)$ is a distance as function of time, t.

8. The method according to claim 1, wherein the partial radial distribution function is $$g_{ij}(r) = \frac{1}{n_0}\frac{n(r)}{4\pi r^2},$$

wherein n(r) is the number density of particles or motifs of type j on distance r from particles of type i and the expression is Previously Presented normalized by the average bulk number density, $n_0$ of type j.

9. A non-transitory computer-readable storage medium containing computer instructions stored therein for causing a computer processor to perform the method of claim 1.

10. An electronic device, comprising: one or more control circuitry; and memory devices storing one or more programs configured to be executed by the one or more control circuitry, the one or more programs including instructions for performing the method of claim 1.

* * * * *